United States Patent [19]

Bamber

[11] Patent Number: 5,538,004
[45] Date of Patent: Jul. 23, 1996

[54] METHOD AND APPARATUS FOR TISSUE-CENTERED SCAN CONVERSION IN AN ULTRASOUND IMAGING SYSTEM

[75] Inventor: Jeffrey C. Bamber, North Andover, Mass.

[73] Assignee: Hewlett-Packard Company, Palo Alto, Calif.

[21] Appl. No.: 396,293

[22] Filed: Feb. 28, 1995

[51] Int. Cl.$^6$ ........................................ A61B 8/12
[52] U.S. Cl. ........................ 128/662.06; 128/916
[58] Field of Search ............... 128/660.07, 660.09, 128/661.01, 661.04, 662.02, 662.06, 916; 607/122

[56] References Cited

U.S. PATENT DOCUMENTS

| | | | |
|---|---|---|---|
| 4,471,449 | 9/1984 | Leavitt et al. | 364/577 |
| 4,821,731 | 4/1989 | Martinelli et al. | 128/662.06 |
| 5,197,037 | 3/1993 | Leavitt | 367/11 |
| 5,222,501 | 6/1993 | Ideker et al. | 128/662.06 |
| 5,322,067 | 7/1994 | Prater | 128/660.07 |
| 5,391,199 | 2/1995 | Ben-Haim | 607/122 |

OTHER PUBLICATIONS

Ch. M. Gros et al, Senologia, Juin 1978, No. 2, pp. 3–14.
N. Shinozuka et al, WFUMB '94 and WFS '94 Abstracts, Ultrasound Med. Biol., vol. 20, p. S267.
D. Rotten et al, BMUS Bulletin, Nov. 1992, British Medical Ultrasound Society, London, pp. 18–23.
A. Moshkalik et al, Abstracts, Ultrasonic Imaging and Tissue Characterization Symposium, 1994, Ultrasonic Imaging, vol. 16, pp. 47–48.
P. R. Detmer et al, Ultrasound and Medicine in Biology, vol. 20, No. 9, pp. 923–936, 1994.
M. D. Handschumacher et a, J. Am. Coll. Cardiol., vol. 21, No. 3, Mar. 1, 1993, pp. 743–753.
G. E. Mailloux et al, IEEE Trans. Med. Imag., vol. 8, 1989, pp. 143–153.
L. N. Bohs et al, IEEE Trans, BME, vol. 38, 1991, pp. 280–286.
Hoskins P. R. et al, European J. Ultrasound, vol. 1, 1994, pp. 159–169.

Primary Examiner—George Manuel

[57] ABSTRACT

A method and apparatus for ultrasound imaging utilize tissue-centered scan conversion to compensate for transducer motion. A reference point, typically located in a region of interest, is selected. An ultrasound probe is positioned at a selected probe position and orientation relative to the region of interest. The region of interest is ultrasonically scanned, and echo signals representative of ultrasound echoes received from the region of interest are generated. The echo signals are referenced to the probe position and orientation. The probe position and orientation relative to the reference point are determined, typically by a sensing device. The echo signals and the probe position and orientation are transformed to image signals for display. The process is repeated for different probe positions and orientations to obtain a plurality of images. Each of the images is referenced to the selected reference point as the probe position and orientation changes, thereby compensating for transducer motion.

20 Claims, 8 Drawing Sheets

METHOD AND APPARATUS FOR TISSUE-CENTERED SCAN CONVERSION IN AN ULTRASOUND IMAGING SYSTEM

FIELD OF THE INVENTION

This invention relates to medical ultrasound imaging and, more particularly, to ultrasound imaging systems and methods which use tissue-centered scan conversion to compensate for transducer motion or tissue motion, or some combination of transducer and tissue motion.

BACKGROUND OF THE INVENTION

With the aid of real-time sonography, visual observation of the dynamic behavior of tissues in response to externally applied mechanical stress (palpation) can make available diagnostically useful information related to tissue elasticity and high level tissue structure, particularly the connectivity of different tissue structures, which affects the tissue's shear properties. In the case of breast examination, for example, this technique of "ultrasound palpation" has become for some diagnosticians a routine part of the sonographic test procedure. The elastic properties of the tissue are often discussed in terms of "mobility" and "compressibility", both of a suspicious region and of its immediate surroundings. The information so obtained can enhance the ability of ultrasound imaging to contribute to detection and differential diagnosis of tumors.

The use of digital ultrasonic echo processing methods, in combination with either controlled externally induced tissue displacement or with naturally occurring cardiac motion, to quantify this motion, image it and measure a tissue elastic modulus has also been of interest. This approach has involved the investigation of a wide variety of both processing techniques and methods of applying the force to the tissue. In general, the force which produces the tissue displacement may be applied manually or automatically.

All currently available real-time ultrasound imaging systems display their image data using a coordinate system which is defined by an origin whose reference is fixed with respect to the transducer. Thus, whether a visual inspection of real-time images or a digital processing method is employed for elasticity studies, if the tissue displacement is produced by moving the ultrasound probe (which may be a transducer array or a mechanical scan head), there is a global image transformation (translation and/or rotation) which is due to the varying relationship between the fixed reference point and the tissue structures. If the movement is large enough, as is often the case with manually induced motion, this effect may interfere with the ability of a visual or numerical analysis to identify the local motion (and therefore elastic) anomalies which comprise the diagnostic information.

Other problems generated by the conventional approach to scan conversion for real-time ultrasound imaging systems are that skilled operation is required to avoid "transducer shake" (the ultrasonic equivalent of camera shake) during detailed study of stationary tissue structures, especially in high resolution scanning modes, and that the effort required to hold the transducer still and/or visually compensate for the moving scene may result in operator fatigue. With the current trend toward very high frequency (20–150 Mhz), very high resolution imaging of intravascular and superficial structures, the problems of transducer shake are likely to increase in severity to a point where they will compromise the resolution potentially available for these devices. Another manifestation of transducer shake is the "flash artifact" on color Doppler images. Finally, full advantage cannot be taken of image enhancement procedures, such as temporal averaging and compounding, since translations and rotations due to transducer motion will blur the average imaged information.

Prior to the introduction of high quality, real-time ultrasonic imaging using hand-held automatic scanning systems, ultrasonic imaging was conducted using static B-scanners. The images, which were not real-time, were generated by manually moving a single element transducer to steer and/or translate the ultrasound beam. The images were displayed via a scan converter using display coordinates that were located in the tissue. It was possible for a skillful operator to produce images which contained global motion corrected elastic information. See, for example, Ch. M. Gros et al, *Senologia*, Juin 1978, No. 2, pps. 3–14. However, because of the static nature of the images, it was not possible to separate time and spatial information. Both were incorporated in a complex manner within a single image.

Three-dimensional imaging and visualization systems, utilizing a two-dimensional ultrasound imaging system and a position and orientation sensing system to construct a three-dimensional image, have been proposed. N. Shinozuka et al in *WFUMB '94 and WFS –94* Abstracts, Ultrasound Med. Biol., Vol. 20, page S267 describe the use of an accelerometer/velocity sensing type of device to sense the position and orientation of a transducer. D. Rotten et al in BMUS Bulletin, November 1992, British Medical Ultrasound Society, London, pps. 18–23 refer to the use of a mechanical sensing arm to provide the position and orientation of a transducer. A. Moskalik et al in *Abstracts, Ultrasonic Imaging and Tissue Characterization Symposium*, 1994, *Ultrasonic Imaging*, Vol. 16, pps. 47–48 describe how information as to the position and orientation of the transducer may be derived from the image data itself. P. R. Detmer et al in *Ultrasound and Medicine in Biology*, Vol. 20, No. 9, pps. 923–936, 1994 describe the use of a "pulsed magnetic field" type of space tracker for sensing the position and orientation of the transducer in a three-dimensional ultrasound imaging system. M. D. Handschumacher et al in *J. Am. Coll. Cardiol.*, Vol. 21, No. 3, Mar. 1, 1993, pps. 743–753 describe the use of a spark gap type of space tracker to sense the position and orientation of a transducer in a three-dimensional ultrasound imaging system.

SUMMARY OF THE INVENTION

According to the present invention, a method for ultrasound imaging of a region of interest of a patient is provided. The method comprises the steps of (a) providing a real-time ultrasound scanning system including an ultrasound probe, (b) selecting a reference point for imaging, (c) positioning the ultrasound probe at a selected probe position and orientation relative to the region of interest, (d) ultrasonically scanning the region of interest and generating echo signals representative of ultrasound echoes received from the region of interest, the echo signals being referenced to the probe position and orientation, (e) determining the probe position and orientation relative to the reference point, (f) transforming the echo signals and the determined probe position and orientation to image signals representative of an image of the region of interest that is referenced to the selected reference point, and (g) displaying the image.

The method preferably further includes repeating steps (c) through (g) for a plurality of probe positions and orientations to obtain a plurality of images. Each of the images is referenced to the selected reference point as the probe position and orientation changes.

In one embodiment, the echo signals and the determined probe position and orientation are transformed to image signals by directly converting the echo signals to image signals that are referenced to the selected reference point. In another embodiment, the echo signals and the determined probe position and orientation are transformed to image signals by converting the echo signals to intermediate image signals representative of an intermediate image that is referenced to the probe position and orientation, and converting the intermediate image signals to the image signals that are referenced to the selected reference point.

The step of determining the probe position and orientation may include sensing the probe position and orientation with a sensing device. In one embodiment, the probe position and orientation are sensed with a magnetic space tracking device. In another embodiment, the probe position and orientation are determined by analysis of the echo signals. When the echo signals are used for this purpose, then the invention may compensate for global tissue motion, or a combination of probe and tissue motion.

According to another aspect of the invention, apparatus for ultrasound imaging of a region of interest of a patient comprises a real-time ultrasound scanning system, including an ultrasound probe for ultrasonically scanning the region of interest when the probe is positioned at a selected probe position and orientation relative to the region of interest, and generating echo signals representative of ultrasound echoes received from the region of interest. The echo signals are referenced to the probe position and orientation. The apparatus further comprises a device for determining the probe position and orientation relative to a selected reference point, a scan converter responsive to the real-time ultrasound scanning system and the device for transforming the echo signals and the determined probe position and orientation into image signals representative of an image of the region of interest that is referenced to the selected reference point, and a display unit responsive to the image signals for displaying the image.

BRIEF DESCRIPTION OF THE DRAWINGS

For a better understanding of the present invention, reference is made to the accompanying drawings, which are incorporated herein by reference and in which.

DETAILED DESCRIPTION

Figure 1:
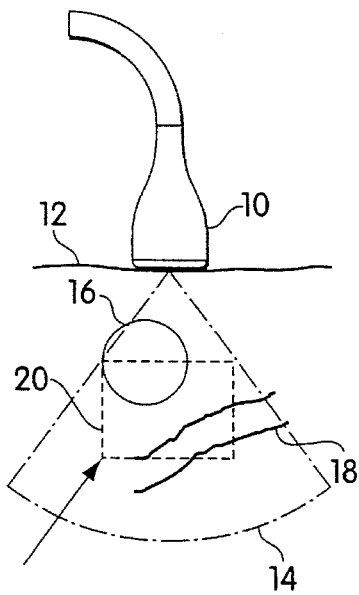
FIG. 1 is an illustration of a first ultrasound probe position and the region scanned by the probe.

The present invention overcomes the problems of conventional scan conversion described above by altering the conventional scan conversion process so as to generate a display whose fixed reference, instead of being relative to the transducer, is assigned to a position and orientation within the tissue. Transducer rotational and translational motion is monitored and is used to update the display so that each real-time frame is compensated for the resulting global image transformations. Real-time tomographic images displayed in this manner, where the fixed reference is tissue-centered rather than transducer-centered, are more suited to both visual and numerical analysis of soft tissue movement in response to transducer motion, and to the application of motion enhancement processing, such as temporal averaging (often known as "persistence"). Tissue-centered scan conversion in accordance with the invention is compared with conventional scan conversion in FIGS. 1–4. In FIG. 1, an ultrasound probe 10 is positioned on a patient 12 in a first position and orientation. The probe 10 is connected to a real time ultrasound scanner (not shown), which scans a sector-shaped scan region 14. Features 16 and 18 are representative of body structures located within scan region 14. A region of interest 20 is defined within scan region 14.

Figure 2:
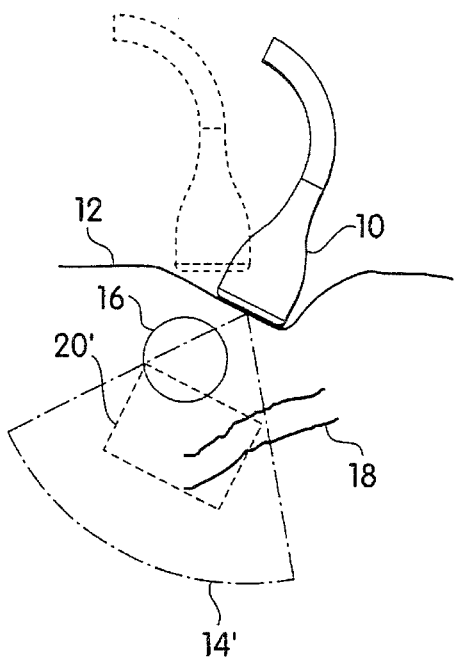
FIG. 2 is an illustration of a second probe position and the region scanned by the probe.

Referring now to FIG. 2, the probe 10 is moved to a second position and orientation and scans a sector-shaped scan region 14', which is translated and rotated relative to scan region 14. This translation and rotation is, in general, three dimensional. However, for clarity, FIGS. 1 and 2 illustrate the situation in two dimensions. It is assumed that features 16 and 18 are not displaced or distorted by the movement of the probe 10. A region of interest 20' within scan region 14' is translated and rotated relative to region of interest 20.

Figure 3:
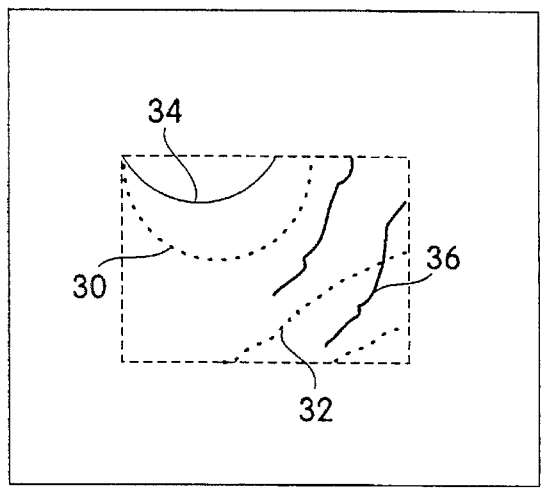
FIG. 3 shows the ultrasound image frames for the first probe position (dotted) and the second probe position (solid) using conventional scan conversion.

Referring now to FIG. 3, the image frames obtained with conventional scan conversion are illustrated. Image elements 30 and 32 represent features 16 and 18, respectively, for the first probe position and orientation shown in FIG. 1. Image elements 34 and 36 represent features 16 and 18, respectively, for the second probe position and orientation shown in FIG. 2. It can be seen that the image elements are translated and rotated between the image frames in response to probe movement.

Figure 4:
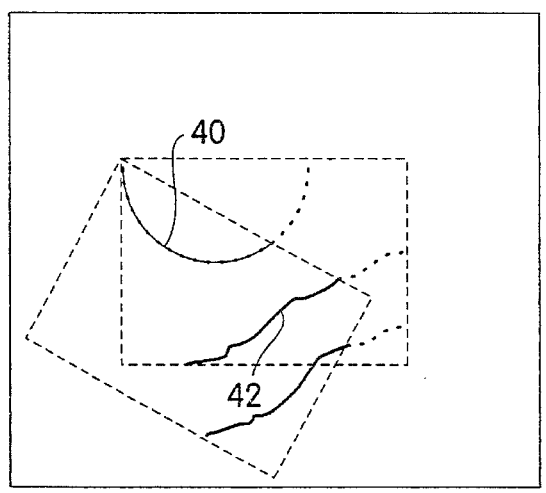
FIG. 4 shows the ultrasound image frames for the first probe position (dotted) and the second probe position (solid) using tissue-centered scan conversion in accordance with the present invention.

Referring now to FIG. 4, the image frames obtained with tissue-centered scan conversion in accordance with the present invention are shown. For each probe position and orientation, the image is arbitrarily referenced to region of interest 20, which remains stationary. Since the image is referenced to a fixed position or region in the tissue, the image elements remain fixed in position on the display screen. More particularly, image elements 40 and 42, which represent features 16 and 18, respectively, remain fixed in position on the display screen despite probe movement. FIG. 4 also illustrates the fact that portions of the stationary region of interest may shift outside the scan region as the probe 10 is moved.

Tissue-centered scan conversion in accordance with the present invention provides a number of improvements in ultrasound imaging of stationary tissue. By easing the visual task of the observer, who no longer has to look at and mentally compensate for scene changes which are due to transducer shake, real-time tissue-centered scan conversion reduces observer fatigue and improves observer performance. By automatically compensating for transducer shake, the technique (a) reduces the level of skill required to hold the transducer still, and (b) eases the muscle fatigue associated with keeping the transducer still during lengthy examination times. By maintaining the registration of displayed tissue structures from one image frame to another, the technique permits echo averaging or other echo combination algorithms (e.g., peak write) to work effectively to improve outlining of tissue structures and reduce speckle noise through compounding. By maintaining the registration of the displayed two-dimensionally projected three-dimensional tissue structures, a much better appreciation of the three-dimensional tissue space is obtained, particularly if the method is combined with temporal averaging, in which case the process reduces to an interactively controlled "summed voxel projection" volume rendered version of the three-dimensional echo information.

Figure 5:
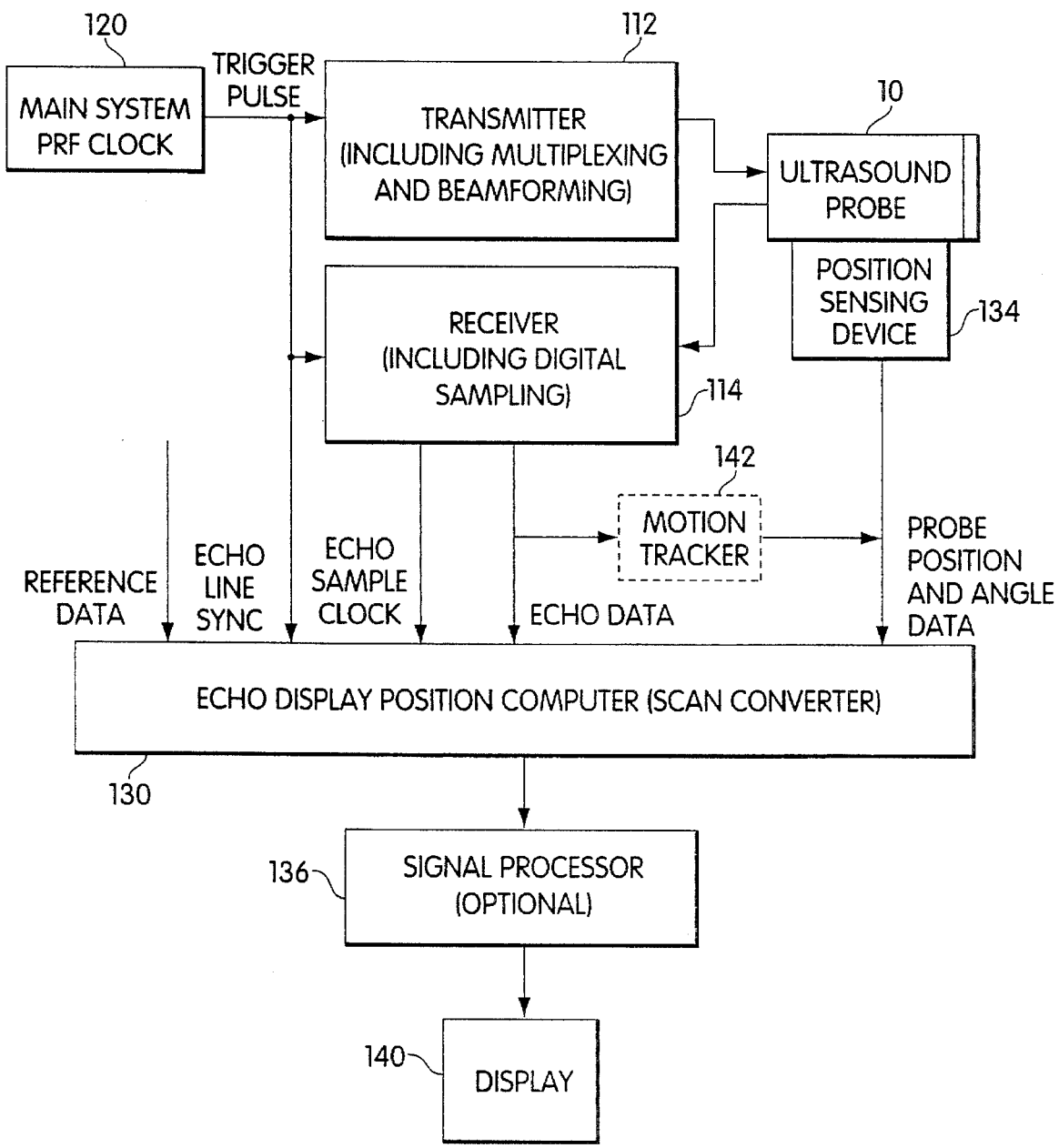
FIG. 5 is a block diagram of apparatus for ultrasound imaging in accordance with the present invention.

A block diagram of apparatus for ultrasound imaging in accordance with the present invention is shown in FIG. 5. Apparatus for real-time ultrasound imaging in accordance with the present invention includes a number of elements that are common to a conventional real-time ultrasound imaging system. An ultrasound probe 10 may include multiple transducer elements in a linear or curvilinear array. Alternatively, the ultrasound probe 10 may include a single transducer element that is rapidly moved by a suitable mechanical actuator to simulate a transducer array. A transmitter 112 and a receiver 114 are connected to the ultrasound probe 10 through a transmit/receive switch (not shown). A typical ultrasound probe 10 may have 128 transducer elements, and the transmitter 112 and the receiver 114 each include a number of parallel channels. The number of transmit channels and receive channels varies from system to system and is less than or equal to the number of transducer elements. Each transmitter channel outputs an ultrasound pulse through the corresponding transducer element into the tissue being imaged. The transmitted ultrasound energy is steered and focused by applying appropriate delays to the pulses transmitted from each transducer element, so that the transmitted energy adds constructively at a desired point in the tissue, or by switching to change the group of transducer elements which form the transmit aperture, or by physically translating the aperture by some form of mechanical actuator, or some combination of the above. The transmitted energy is partially reflected back to the ultrasound probe 10 by various structures and tissues in the patient's body in the form of ultrasound echoes.

Steering and focusing of the received ultrasound echoes are effected in a reverse manner. The reflected ultrasound echoes arrive at the transducer elements of probe 10 at different times and are converted by each transducer element to received signals. The received signals are amplified and delayed in separate processing channels and are then combined in a receive beamformer in receiver 114. The beamformer may be analog or digital. The group of transducer elements and the delay for each channel are selected such that the receive beam is steered at a desired angle and is focused at a desired point. The delays may be varied dynamically so as to focus the beam at progressively increasing depths as the ultrasound echoes are received. The transmitted beam is scanned over a region of the patient's body in a desired scan pattern, typically a sector scan or a parallel scan. The outputs of the receiver 114 are echo signals which represent ultrasound echoes received by probe 10 from the region of interest. Typically, the echo signals comprise echo data for multiple points along each scan line in the scan pattern. The receiver 114 may include additional features such as compression, envelope detection, Doppler detection, and the like.

A main system clock 120 generates timing signals for the imaging process. The system clock 120 provides a trigger pulse to transmitter 112 to initiate transmission of an ultrasound pulse for each scan line. The trigger pulse is also used by the receiver 114 to synchronize reception of ultrasound echoes.

A number of techniques for real-time ultrasound imaging are well known to those skilled in the art. An example of a commercially available, real-time ultrasound imaging system that utilizes conventional scan conversion is the Sonos 1500 manufactured and sold by Hewlett-Packard Company. The apparatus of the present invention can utilize conventional components for probe 10, receiver 114, transmitter 112 and main system clock 120.

An echo display position computer, or scan converter, 130 converts the echo data from receiver 114 into image signals for producing an ultrasound image, as described below. In the example of FIG. 5, the echo display position computer 130 replaces the scan converter in a conventional ultrasound imaging systems. The echo display position computer 130 receives reference data, typically selected by an operator, an echo line sync from main system clock 120, an echo sample clock and echo data from receiver 114, and probe position and angle data. As described below, the echo display position computer 130 uses the probe position and angle data to transform the echo information provided by the real-time ultrasound imaging system to tissue-centered image signals. The output of echo display position computer 130 is supplied through an optional signal processor 136 to a display unit 140, typically a video monitor. Signal processor 136 may perform additional operations on the image signals, such as time averaging, or the like.

The apparatus of the invention may include a sensing device 134 for sensing the position and orientation of ultrasound probe 10. The sensing device 134 provides probe position and angle (orientation) data to the echo display position computer 130. The sensing device 134 may be implemented in one of several ways and is shown schematically in FIG. 5.

In one embodiment of the sensing device 134, a space tracking device, which may be electromagnetic, spark gap, optical or some other type, is attached to the ultrasound probe 10. This generates probe position and angle information in the form of three position coordinates and three orientation coordinates relative to a nearby fixed reference. An example of a magnetic space tracking device is the Bird system available from Ascension Technology.

In another embodiment of the sensing device 134, an accelerometer of a type related to those used for automatic video camera shake compensation may be attached to the ultrasound probe 10. The accelerometer generates information which is processed to yield positional and orientational changes which have occurred since a fixed reference time. An example of this type of device is the Gyrostar™, a piezoelectric vibrating gyroscope available from Murata Electronics, Inc. In a further embodiment of the sensing device 134, the ultrasound probe 10 may be attached to a mechanical position and orientation sensing arm, similar to those used with single element transducers in prior art static B-scan systems. This approach provides absolute coordinate data at relatively low cost, but restricts operator access to the scanning space and movement through it.

In a somewhat different approach to determining probe position and orientation, the ultrasonic tissue image data itself, while still in probe coordinates, is analyzed to track global transducer translations and rotations, thus generating positional and orientational changes which have occurred since a fixed reference point in time. Such echo tracking may be performed using radio frequency (RF) or envelope detected echo data and may operate in one dimension, two dimensions or three dimensions. Methods for tracking include published techniques known as "optical flow" correlation based speckle tracking, and the use of multiple-line or multiple angle Doppler information. An optical flow method is described by G. E. Mailloux et al in *IEEE Trans. Med. Imag.*, Vol. 8, 1989, pps. 143–153. An example of correlation based speckle tracking to described by L. N. Bohs et al in IEEE Trans, BME, Vol. 38, 1991, pps. 280–286. A Doppler method is described by Hoskins P. R. et al in European J. Ultrasound, Vol. 1, 1994, pps. 159–169. This method only works to within a level of statistical precision determined by the extent to which local image alterations (due to elastic tissue deformation) upset the image tracking algorithm. This approach may fail if the probe is moved in a direction orthogonal to the scan plane, although the problem may be overcome when three dimensional scanners become available. This approach may be useful, however, in hand-held, very high resolution imaging of superficial structures, such as the skin, where a standoff between the probe and the tissue surface is employed, and tracking of the first entry echo can provide the required reference information. This approach may also be useful if the source of relative motion between the tissue and probe is body movement, or some combination of probe and body motion. For example, in the muscle of the beating heart, small changes in relative tissue displacement may be made more apparent by using this embodiment of the invention to apply compensation for the global motion of the specific region of the heart. When the probe position and orientation are derived from the image data, the sensing device 134 is not required. In this case, a motion tracker 142 generates probe position and angle data from the echo data. The motion tracker 142 includes all pre-processing steps necessary for the tracking method employed, such as envelope detection, Doppler detection, and the like.

Several approaches can be taken to scan conversion computations. In a first approach, the processing is split into two stages. First, the complete image is formed in probe coordinates using only the echo data, the echo sample clock and the echo line sync, as in current real-time ultrasound imaging systems. Second, the probe position and angle data are employed to perform a coordinate transformation, resampling and interpolation of the first image to generate a second image for display in tissue-centered coordinates. The two-step scan conversion is easier to add to existing ultrasound imaging systems. For example, a computer, frame grabber and position and angle sensing device external to the ultrasound imaging system can be utilized. Disadvantages of the two-step approach include accumulation of errors due to multiple stages of processing (resampling and interpolation) of the same data and the redundancy of hardware. In a second approach, the echo data for each scan line is combined as it arrives, with the probe position and angle data, the reference data, the echo line sync and the echo sample clock to form a fully transformed and interpolated image in tissue-centered coordinates. This approach corresponds to the apparatus of FIG. 5. If the probe position and angle data are available only as frequently as the frame rate, there is the potential for image distortions associated with the fact that the probe may have moved during the frame period. In a third approach, beamforming and scan conversion may be combined as described in U.S. Pat. No. 5,197,037, issued Mar. 23, 1993 to Leavitt. Under normal circumstances of operation of medical ultrasound scanners, this mode of operation is unlikely to be necessary. In the future, however, methods known by those skilled in the art as "synthetic aperture" imaging techniques may gain popularity of usage. These methods require separate recording of received echo signals on all transducer elements for ultrasound transmission on each and every transducer element, or group of elements. The time taken to obtain data to reconstruct one image sample by this method may not be negligible compared to the rate of relative motion, and such methods may benefit from motion compensation of the kind described here.

Figure 6:
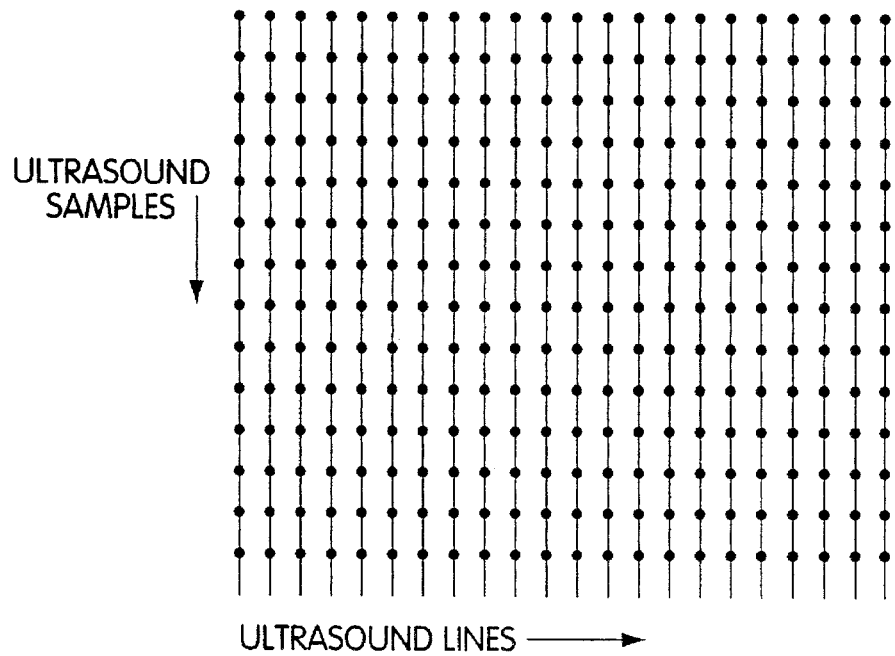
FIG. 6 illustrates a parallel ultrasound scan format.
Figure 7:
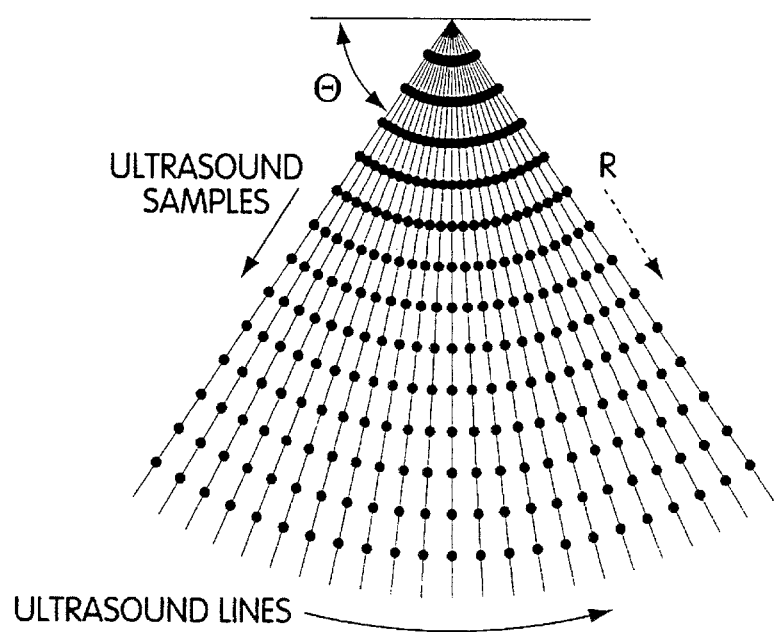
FIG. 7 illustrates a sector ultrasound scan format.

FIGS. 6 and 7 illustrate two different scan and display formats which are generally utilized in real-time ultrasound imaging. With a linear scan as shown in FIG. 6, the scan lines are parallel and generally orthogonal to the plane of the linear transducer array. The spacing of the scan lines is, however, not necessarily directly related to the spacing of the transducer array elements. After beamforming has been completed, the sample values are in an X-Y (rectangular) coordinate system, and conventional scan conversion is a relatively simple interpolation process.

By contrast, with a sector format such as that shown in FIG. 7, information is received in a polar format, which must then be converted to X-Y format for display. With a sector format, each scan line is projected at an angle $\theta$ to the plane of the array. The angle $\theta$ may typically cover $\pm 45°$ in $\frac{3}{4}°$ steps, which may result in 121 scan lines, each containing approximately 400 sample points after beamforming to create a series of samples at constant intervals in range R. This set of samples in R-$\theta$ coordinates is then converted to the X-Y grid coordinates, with a pixel appearing at each X-Y junction of the display. A typical display may have 512×512 lines.

Since the method and apparatus for tissue-centered scan conversion are substantially the same whether a linear format or a sector format is utilized, and since the operation with a sector format is more complicated, the following discussion will be with respect to a sector formatted system. However, it should be understood that what is being said for a sector formatted system applies equally with respect to a linear format or any other arbitrary display format. Further, the method and apparatus for combining beam formation and scan conversion into a single operation in a digital front end have been described previously (Leavitt U.S. Pat. No. 5,197,037). It should be understood that what is being said in the following description of a method and apparatus for tissue-centered scan conversion applies equally with respect to beam formation, when methods such as those described by Leavitt are employed for beam formation.

In the conventional approach, where beam formation and scan conversion are two separate sequential operations, scan conversion can be effected by a wide variety of techniques. For example, the beamformed signals may be sampled at a uniform rate and interpolated to obtain Y-boundary crossings, after which the Y-boundary crossings are interpolated to obtain X-boundary crossings. More elaborate techniques may also be utilized, such as those taught in U.S. Pat. No. 4,471,449, issued Sep. 11, 1984 to Leavitt et al. For the purposes of the following, a general description of the scan conversion operation will be provided. It should be understood that what is being said applies equally with respect to other methods of scan conversion, which primarily differ from the following description and from each other, only in terms of the methods used for sampling or interpolation. It should be further understood that the description applies equally well to all types of echo data, whatever the displayed parameter, whether it be the sampled radio frequency signal itself, the envelope detected echo signal, a component of flow velocity extracted by Doppler processing of a number of repetitions of the same scan line, or parameters resulting from other processing of the echo signal.

Figure 8:
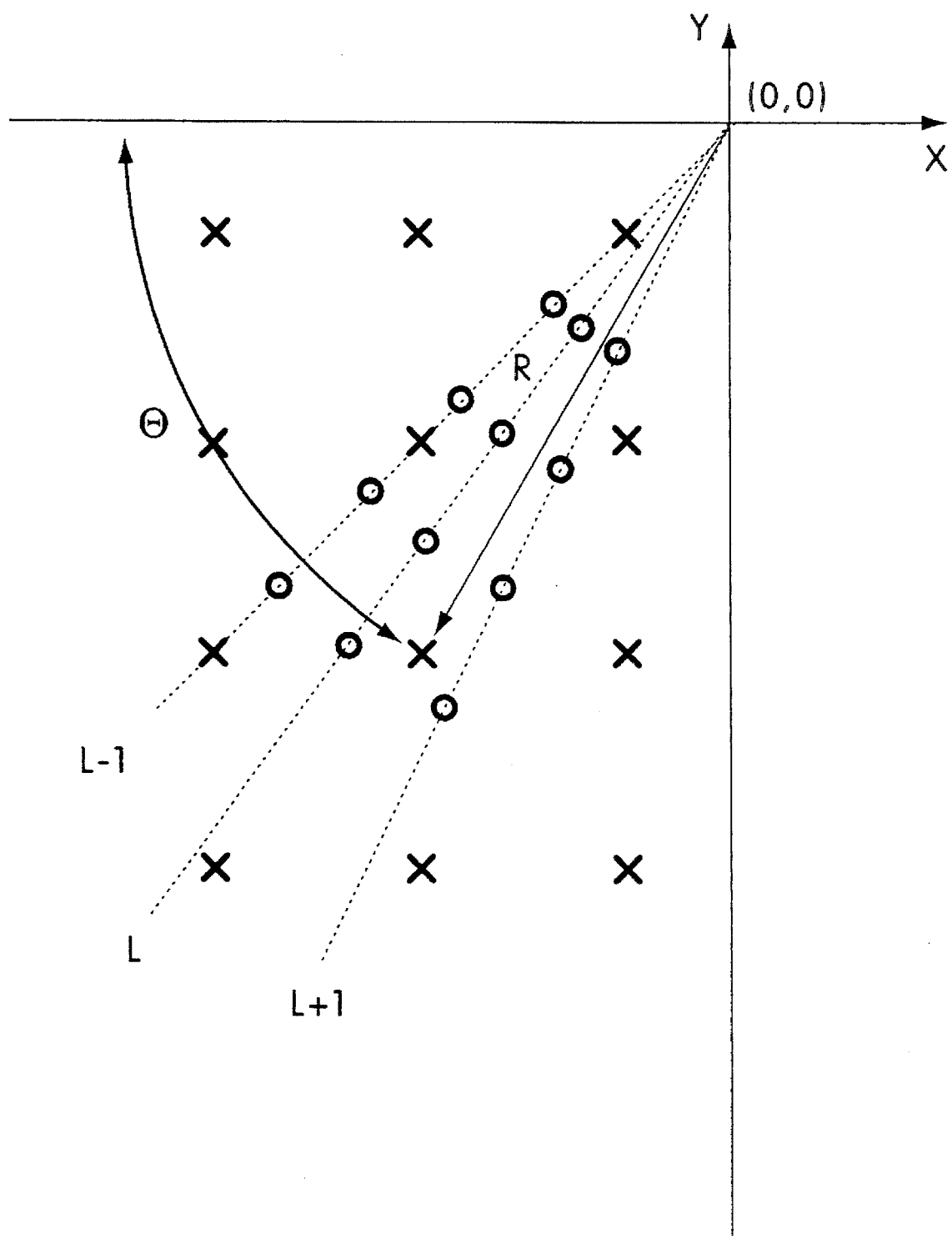
FIG. 8 illustrates the geometry of conventional scan conversion from R-θ coordinates to X-Y coordinates.

Referring to FIG. 8, three illustrative scan lines L, L−1 and L+1 are shown, each of which projects from a (0,0) origin point at an angle r to the plane of the transducer array. For the purposes of the following discussion, the origin point is considered to be the mid-point of the transducer array. The x's in FIG. 8 represent the location of pixel points on the display for displaying a scanned image in X-Y coordinates. In FIG. 8, it is seen that some of the scan lines L may pass through a pixel point, while other pixel points are not intersected by a scan line. For each scan line L, there is a plurality of points at which samples may be taken. The o's in FIG. 8 represent the locations of echo data sample points, obtained at constant intervals along each scan line. There need be no relationship between the sample points and the pixel points, although there may be such a relationship in some scan conversion techniques. The task of scan conversion in its most general form may then be described by the following steps for each pixel point (X,Y). First, the values of R and r corresponding to the pixel point (X,Y) are determined, as shown in FIG. 8. For purposes of this discussion, it is assumed that the spacings between the X and Y display grid lines are expressed as normalized quantities so that R and θ may be calculated from $$R=(X^2+Y^2)^{1/2} \quad (1)$$

and $$\theta=\tan^{-1}(Y/X) \quad (2)$$

This normalization involves a scaling of the time wt between samples of the echo signal along a given line L so that the equivalent samples in range R are spaced at intervals ΔR such that $$\Delta R=cwt/2 \quad (3)$$

where c is the speed at which sound propagates in the medium-. For an ultrasonic medical scanner, it is well-known that c may be considered to be a constant 1540 m/sec. If desired, this value alternatively may be determined for a particular portion of the patient's body being scanned.

The value to be placed at display grid position (X,Y) is then calculated by two dimensional interpolation of N nearest neighboring data samples in polar coordinates to the point (R,θ). The number N is dependent on the interpolation method. The whole process is repeated for all pixels in the display grid. Display pixels whose (R,θ) coordinates correspond to a point outside the scanned area are assigned a value of zero, or some other predefined default value or color.

The above process may also be viewed and implemented in its reverse form where, for each pixel position (X,Y), the coordinates of the N nearest neighboring data samples are determined in X-Y coordinates, by reverse application of equations (1) and (2), and their data values interpolated in X-Y space to obtain a value for the pixel position.

In conventional real-time ultrasound scan conversion, the above procedure, or some version of it differing only in terms of the method used for sampling or interpolation, is employed independent of any relative motion between the transducer and the patient. The origin point (0,0), which was assumed earlier to be at the center of the transducer array, therefore, remains always in a fixed position on the X-Y display grid. As a result when, for example, the transducer is moved, the images of the body structures move on the display. Tissue-centered scan conversion, on the other hand, is designed to provide compensation for this relative motion.

Figure 9:
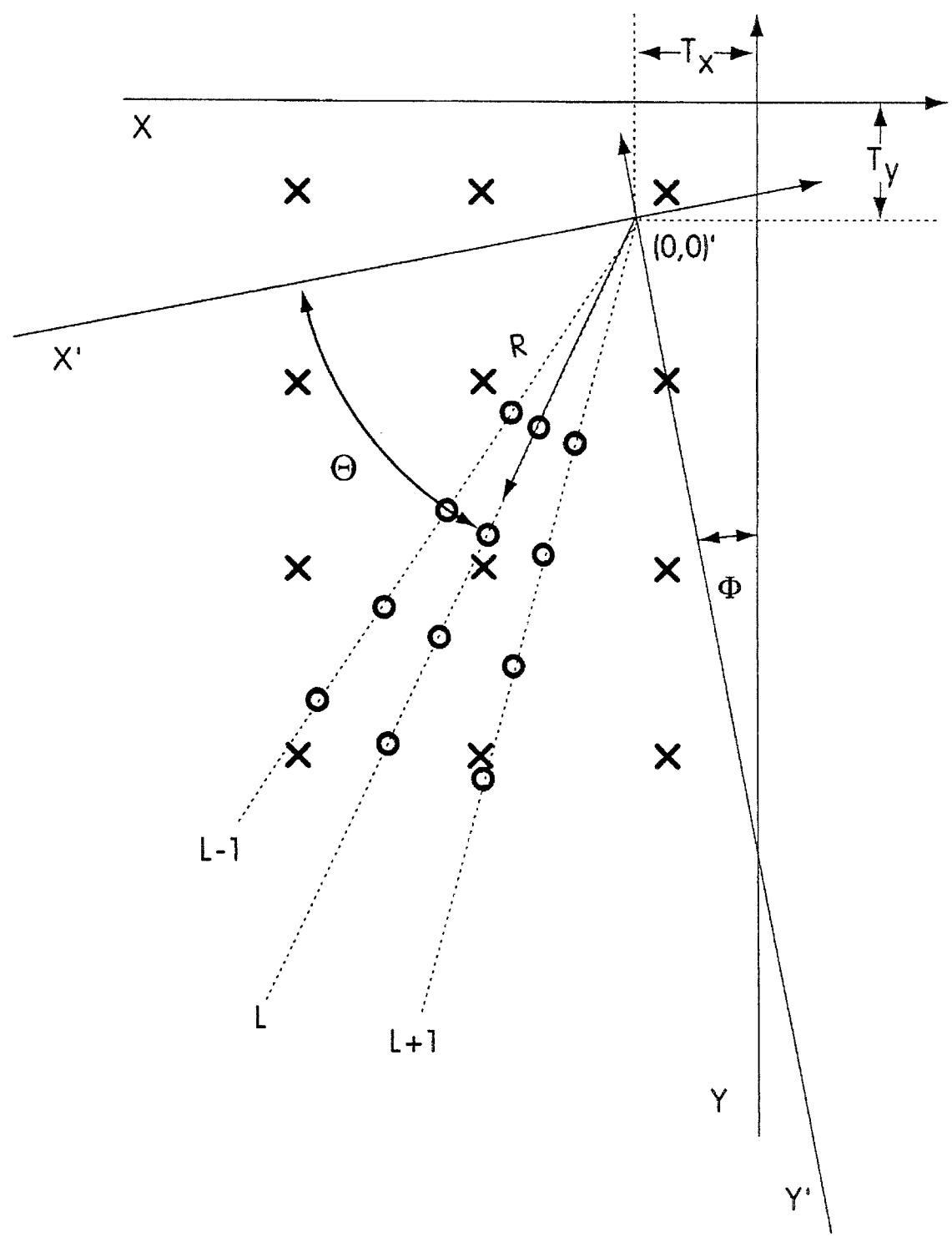
FIG. 9 illustrates tissue-centered scan conversion from R-θ coordinates to X-Y coordinates in accordance with the present invention.

Referring to FIG. 9, the process of tissue-centered scan conversion is described in terms of its relationship to the above description of conventional scan conversion. In the preferred embodiment of the invention, position and angle data are available from a position sensing device attached to the ultrasound probe. Further, also in the preferred embodiment, these data contain information about the position of the transducer array, i.e., the location of the origin point (0,0), and the direction in which the transducer array was pointing, at the time when the echo data for each scan line L was obtained. If the rate of scanning to generate a single frame is sufficiently rapid, or if the relative motion between the patient's body and the probe is sufficiently slow, it is possible to assume that all scan lines within a given frame are associated with approximately the same position and angle data, such that the data from the position sensing device need only be sampled once per frame. For simplicity of the drawing, this is the situation illustrated in FIG. 9. However, for purposes of describing the workings of the invention, the flow diagram of FIGS. 10A and 10B assumes the more general case in which the position and angle data are updated for each scan line L.

Figure 10A:
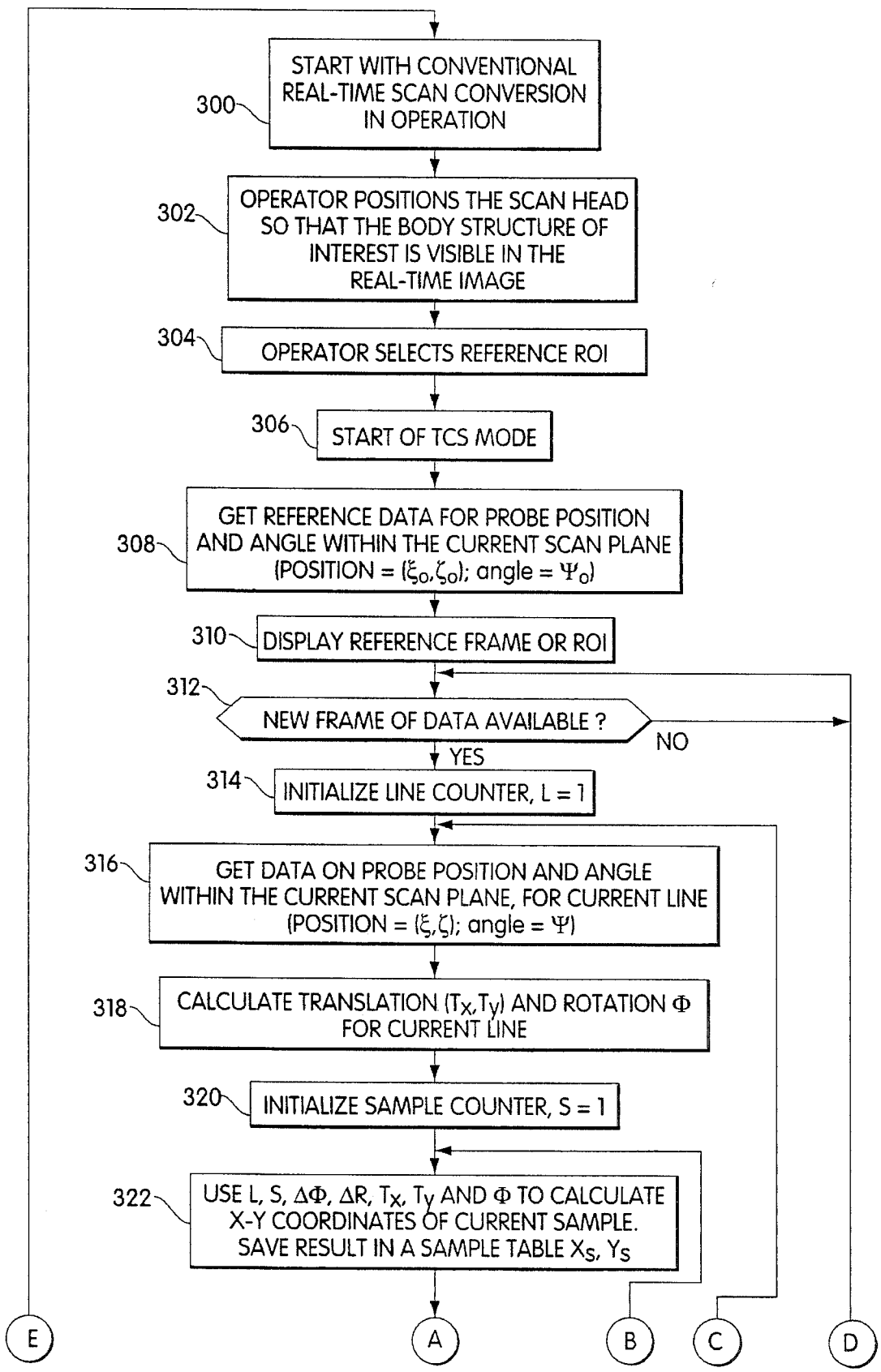
FIG. 10A and 10B show is a flow diagram of tissue-centered scan conversion in accordance with the present invention.
Figure 10B:
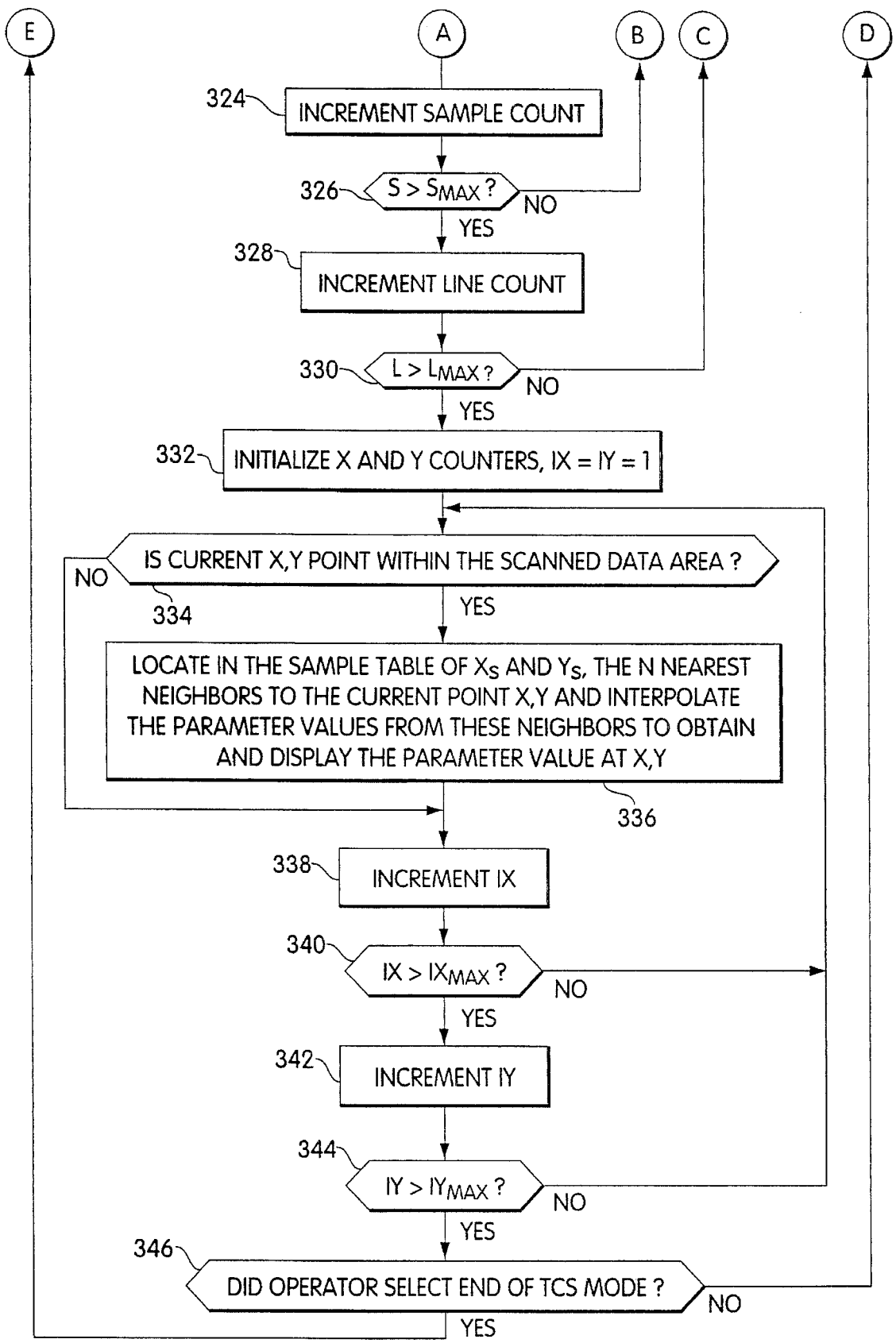

Referring to FIGS. 10A and 10B, the procedure begins with the scan converter operating in a conventional mode (step 300). The operator positions the transducer array (ultrasound probe 10) so that the body or object structure of principal interest is visible in the real-time image (step 302). The operator then selects a reference point or a region of interest (ROI) within the body (see FIG. 1) by indicating its coordinates on the X-Y grid of the currently displayed image (step 304). The ROI may be as large as the whole scan frame if desired. The reference point or ROI may, for example, be selected with a trackball or other pointing device conventionally used in ultrasound imaging systems. When the operator selects a region of interest, a point within the ROI functions as the reference point for tissue-centered scan conversion.

The system then begins the tissue-centered scan (TCS) mode of operation (step 306). This mode begins by sampling reference data for the current position, $(\xi_0, \zeta_0)$ and orientation, $\psi_o$, that defines the initial relationship between the tissue and the probe within the plane of the current scan (step 308), and displaying the current ROI on the screen in the fixed position as would the conventional scan converter (step 310). This display of the reference ROI defines the position and orientation of the X and Y axes, as illustrated in FIGS. 8 and 9.

The position $(\xi_0, \zeta_0)$ and orientation $\psi_o$ may be derived by various means, depending on the particular embodiment, of the invention. In the preferred embodiment a "space tracker" type of device, such as The Flock of Birds™, (Ascension Technology Corporation, Burlington, Vt.), is used. Such devices may provide the position and orientation data in their own, possibly three dimensional, coordinate system. For the sake of simplicity of illustration of the invention, FIGS. 8 and 9 assume a two dimensional situation and two dimensional motion of the probe, such that when relative motion occurs between the probe and the body, the translation $T_x$ and $T_y$ and rotation $\phi$, of the axes (see X' and Y' in FIG. 9) may be computed as $$T_x=\xi-\xi_0, T_y=\zeta-\zeta_0 \text{ and } \phi''=\psi-\psi_0 \quad (4)$$

When the reference ROI has been displayed, the operation proceeds to determine if a new frame of echo and position data has been made available (step 312). This is primarily a synchronization step to enable the system to wait for all data necessary for the interpolation procedure to be available in a buffer memory within the echo display position computer 130, which temporarily stores the sequence of echo lines and corresponding probe position and angle data. Processing to display this frame or ROI of echo data using tissue-centered scan conversion then proceeds by two sequential loops of operations. The first loop begins by initializing a line counter (step 314), so that line 1 of the echo data is the first to be operated upon. Probe position ($\xi$, $\zeta$) and angle c data corresponding to this line are then retrieved from the buffer memory (step 316). These data are then used to compute the within-plane components of the probe translation $T_x$ and $T_y$, and rotation, $\phi$, appropriate to this scan line, as illustrated for any of the scan lines in FIG. 9 (step 318). An inner loop of operations is now executed to process each of the echo signal samples along this scan line, beginning by initializing the sample counter to the first sample, S=1 (step 320). The next step is to calculate the display position for this sample in X-Y coordinates, accounting for the probe motion that was recorded for this scan line (step 322). The scan angle $\theta$ is given by $\theta=(L-1)\Delta\theta$ is the angular separation between scan lines and $\theta_0$ is the scan angle for the first line. The sample range R is given by $R=(S-1)\Delta R+R_0$, where $\Delta R$ is obtained from Equation (3) and $R_o$ is the range for the first sample, given by $t_o c/2$, where $t_o$ is the delay between the time of the transmit pulse and the time for the first sample. The X-Y coordinates for the current sample $(X_s, Y_s)$ are then obtained from $$X_s=T_x+R\cos(\theta+\phi) \quad (5)$$

and $$Y_s=T_y+R\sin(\theta+\phi) \quad (6)$$

The values of $X_s$ and $Y_s$ are then saved in a table, which is linked with the corresponding set of sample values of the echo parameter, so that the X-Y display position of any sample may be retrieved. The sample count S is then incremented (step 324) and checked against a preset maximum $S_{max}$ (step 326), which determines the maximum number of samples along a line. If the maximum has not been reached, the process returns to calculate and store $X_S$ and $Y_S$ for the next sample along the line. This is repeated until $X_s$ and $Y_s$ values have been computed for all samples along the current line, after which the line counter L is incremented (step 328) and checked against a preset maximum $L_{max}$ (step 330), which determines the maximum number of scan lines in a frame. If this maximum has not been reached, the process returns to calculate $X_s$ and $Y_s$ values for all samples on the next line, using new data for $T_x$, $T_y$, $\theta$ and $\phi$. This is repeated until $X_s$ and $Y_s$ values have been computed for all samples along all lines.

At this point in the process the second loop begins, following initialization of X and Y counters, IX and IY, to 1 (step 332). The function of this loop is to reconstruct and display all pixels of the tissue-centered scan converted image frame, by interpolation of the recorded echo parameter sample values. Pixel position IX=1, IY=1 may correspond, for example, to the top left corner of the X-Y display grid. By examination of the set of values for $X_S$ and $Y_S$ for the current frame, step 334 determines whether this pixel position lies within the currently scanned data area for the ROI. If it does not, then step 336 is skipped, and IX is incremented to select the next pixel position in sequence (step 338). If, however, the current pixel position is within the current ROI, then the next step is to examine the table of $X_S$ and $Y_S$ values to find its N nearest neighbors (step 336). The parameter value at the current X-Y pixel position is then displayed, after being calculated by interpolation from these N nearest neighbors, according to one of many published interpolation methods, where N is dependent on the interpolation method employed, as described earlier for conventional scan conversion. IX is then incremented (step 338), and the process repeats to calculate the interpolated parameter value for the next X-Y pixel position until all pixels along a row of the display have been dealt with (step 340), after which IY is incremented (step 342), and the process repeats once again until all values for all pixels along all rows have been computed and displayed (step 344). At this point, the display will contain a new frame of data, displayed using tissue-centered scan conversion. It is possible at this point to return and wait for a new frame of data to become available, or to exit TCS mode and return to display in a conventional scan conversion mode (step 346).

As indicated previously, the motion correction may be applied after conventional scan conversion has taken place. This requires the probe position and angle data to be sampled once per scan frame, assumes that the motion is slow enough to permit this to be done without substantial artifact due to motion during the scan time for a single frame (although this artifact is already present with conventional scan conversion) and reduces to a transformation of one X-Y display coordinate system to a translated and rotated version of the same coordinate system. This is a standard problem in image processing (see, for example, J. D. Foley et al, *Fundamentals of Interactive Computer Graphics,* Addison-Wesley, Reading, 1982) and, using the same notation as for equations (5) and (6), the new screen coordinates (X', Y') for a pixel at position (X,Y) in the reference ROI, after probe rotation in the scan plane by an angle d and translation in the scan plane by a vector with components $T_x$ and $T_y$ will be:

$$X'=(X\cos\phi=Y\sin\phi)+T_x \quad (7)$$

and $$Y'=(X\sin\phi Y\cos\phi)+T_y \quad (8)$$

In another alternative embodiment, the motion compensation could, in principle be applied after beam formation but where new information on position and orientation is available more rapidly than the once per scan line implied by the flow diagram of FIGS. 10A and 10B. The limit for motion compensation to be applied at this stage would be one position and orientation data sample per beam formed echo sample. Under normal circumstances of operation of ultrasound scanners (depth of imaging and rate of probe or other motion), it is relatively unlikely that such rapid sampling would be necessary.

There are many ways in which the procedure may be modified to deal with the more general case of three dimensional probe motion. In one embodiment, steps 308, 316, 318 and 322 may be modified so as to perform the calculation of $X_s$ and $Y_s$, for each echo sample, according to the following method.

Figure 11:
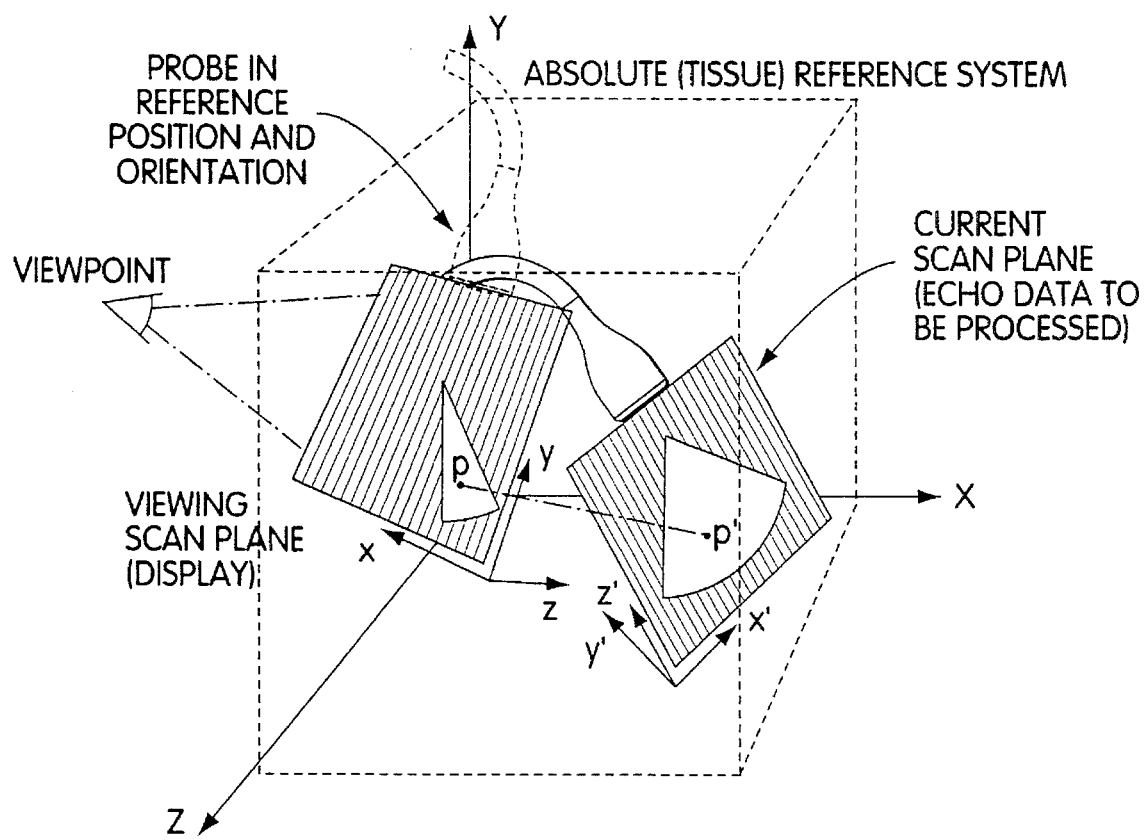
FIG. 11 illustrates the geometry of the three dimensional case.

FIG. 11 illustrates the three dimensional case where a point P (not shown) now refers to a position in three dimensional space (X,Y,Z) referenced to the tissue. Referring to FIG. 11, the point p' represents the position of the current echo sample (x', y', 0) within the current scan plane, after (if necessary) converting its (R,θ) coordinates to (x',y') coordinates according to the conventional scan conversion equations (1), (2) and (3). The point p represents the position of this same echo sample (x,y,z) within the scan plane obtained when the probe is in its reference position and orientation (step 308). This scan plane is termed the viewing (or display) plane. The desired values of $X_s$ and $Y_s$ are obtained as scaled values of the x and y coordinates of point p, ignoring its z coordinate. For the description of three dimensional transformations, it is common practice and convenient to use vector and matrix notation. P, p' and p are then vectors whose elements are their three corresponding coordinate values. Step 308 then corresponds to obtaining from the position sensing device 134 an offset vector, $O_{view}(X,Y,Z)$, and a 3×3 rotation matrix, $M_{view}$, which describe the position and orientation of the viewing plane with respect to the point in the tissue when the probe is in its reference position and orientation. Step 316 corresponds to obtaining from the position sensing device 134 an offset vector, $O_i(X,Y,Z)$, and a 3×3 rotation matrix, $M_i$, which describe the position and orientation of the scan plane for the current scan line L. In the preferred embodiment, where a pulsed magnetic field type of space tracker is used as the position sensing device, a small magnetic receiver is attached to the probe. This provides values for $O_{view}(X,Y,Z)$, $O_i(X,Y,Z)$, $M_{view}$ and $M_i$, for its own position and orientation with respect to a magnetic transmitter that is fixed in relationship to the tissue. The receiver may, however, be slightly offset and rotated with respect to the ultrasound scan plane and origin (0,0)' (see FIG. 9), such offset and rotation being described by a calibration offset vector $O_{cal}(x', y', z')$ and 3×3 rotation matrix $M_{cal}$. Step 318 may then be omitted and step 322 replaced by the following calculation of $X_s$ and $Y_s$, described here in two stages. Stage one involves determining the (X,Y,Z) coordinates of the current echo sample. This amounts to transforming the vector p' to the vector P, using an equation such as $$P=O_i+O_{cal}M_i+p'M_{cal}M_i$$

where the additions and multiplications imply vector and matrix additions and multiplications. Stage two requires determination of the (x,y,z) coordinates of the current echo sample by transforming the vector P, obtained from the above equation, to the vector p, using an equation such as $$p=(P-O_{view}-O_{cal}M_{view})M_{view}^{-1} M_{cal}^{-1}$$

Finally, as mentioned above, $X_S$ and $Y_S$ are given by the x and y elements of the vector p, after scaling by a factor that is fixed for a given display.

Various alternatives to the above scheme are possible. It may, for example, be possible to implement the method described by FIGS. 9, 10A and 10B even when the motion is three dimensional, so long as the translation $T_x$, $T_y$ and rotation φ within the viewing plane are calculated using the full three dimensional probe position and orientation information and so long as the length of the scan line L within the viewing plane, and the sample interval ΔR within the viewing plane, used to calculate R in equations (5) and (6), are adjusted for the three dimensional orientation of the current scan line with respect to the viewing plane.

For the preferred embodiment, motion correction was described as being applied to each and every scan line, after beam formation. This would require the invention to be implemented as modifications to the hardware and software of a conventional real-time scan converter. Hardware modifications would be required to enable the scan converter to read and store data on the probe position and angle, synchronized with the echo line acquisition rate of the system. In some scan conversion systems, additional input buffer memory might also be required if, for example, the system routinely buffers only a limited number of lines of echo data before scan conversion. Ideally, if rapid motion is to be accommodated, all echo lines for a complete frame would be available from a buffer memory prior to scan conversion. It is assumed in the flow diagram of FIGS. 10A and 10B that, at the step which queries whether a new frame of data is available (see the first small loop), such a complete frame buffer is present in the hardware. Finally, additional memory may also be required, with associated hardware and software, to store and retrieve the coordinates $X_S$ and $Y_S$ (see FIGS. 10 and 10B). The calculations indicated in FIGS. 10A and 10B may be executed by one or more general purpose computer processors attached to the appropriate memory, data buses and input-output devices. Alternatively, and more likely for real-time implementation, dedicated special purpose integrated circuits, such as Pythagoras processors, may be employed for one or more of the calculations involved. Many of the remaining components of a conventional scan converter, such as output buffer memory, the serializer, look-up table and digital to analog converter, need not be modified.

The preferred embodiment assumes that the probe moves independently of the tissue. If, however, the probe is in contact with the tissue then probe motion will cause tissue motion. The assumption of independence is an approximation which increases in accuracy the deeper the ROI. It is also likely to be true for ROIs which are immediately anterior to an immovable boundary, such as bone.

Under circumstances where this approximation is not good, then two possible solutions are known to exist. Firstly, the alternative embodiment of the invention, in which the echo motion tracker is employed rather than a device attached to the probe, will provide the correct result for a sufficiently localized ROI, within the statistical approximation of this method as described above. Secondly, an extension to the invention may be envisaged in which the average rate of decay of the tissue displacement with depth is estimated from a theoretical model of tissue mechanical properties, so that, for the depth at which the ROI exists, the tissue displacement due to probe pressure may be calculated and substracted from T, before calculating the tissue centered scan converted display.

Tissue-centered scanned conversion of real-time tomographic ultrasound scans in accordance with the present invention offers the following specific advantages over conventional scan conversion systems:

1. Easier visualization of localized motion anomolies related to tissue elasticity and connectivity without the confusing effects of global seen motion;

2. A rational starting point for the application of numerical methods of analyzing tissue motion and generating elasticity images, so that large tissue displacements may be employed without loss of spatial resolution in the elasticity images due to global motion blurring;

3. Elimination of transducer shake in routine ultrasound imaging when it is necessary to carefully study a specific stationary region of the body (especially in the "high resolution" mode which some manufacturers are now offering), resulting in reduced motion blur, reduced observer fatigue, reduced muscular fatigue and reduction in the skill required to operate the system. This may become an increasingly important advantage with the further development of intracavity and very high resolution (microscopic) ultrasound imaging devices;

4. An alternative approach to removing the flash artifact from color Doppler images of blood flow; and 5. A starting point for the application of other image improvement procedures, such as compounding.

With tissue-centered scanned conversion running in real-time and in combination with either persistence (a running weighted averaging) or with an unweighted time average for a fixed time interval, the ultrasound imaging system can be used for (a) interactive tissue elasticity enhancement (since rigid structures remain sharp), (b) interactive volume-rendered imaging (since the algorithm then reduces to the "summed voxel projection" method of volume rendering), and (c) interactive single plane or volume compounding.

While there have been shown and described what are at present considered the preferred embodiments of the present invention, it will be obvious to those skilled in the art that various changes and modifications may be made therein without departing from the scope of the invention as defined by the appended claims.

What is claimed is:

1. A method for ultrasound imaging of a region of interest of a patient, comprising the steps of:
   a) providing a real-time ultrasound scanning system including an ultrasound probe;
   b) selecting a reference point for imaging;
   c) positioning the ultrasound probe at a selected probe position and orientation relative to the region of interest;
   d) ultrasonically scanning the region of interest by transmitting an ultrasound beam from said ultrasound probe, automatically steering the ultrasound beam with respect to said ultrasound probe and generating echo signals representative of ultrasound echoes received from the region of interest in response to the transmitted ultrasound beam, said echo signals being referenced to said probe position and orientation;
   e) determining said probe position and orientation relative to said reference point;
   f) transforming the echo signals and the determined probe position and orientation to image signals representative of an image of the region of interest that is referenced to said selected reference point; and
   g) displaying said image.

2. A method as defined in claim 1 further including repeating steps c)- g) for a plurality of probe positions and orientations to obtain a plurality of images, whereby each of said images is referenced to said selected reference point as the probe position and orientation changes.

3. A method as defined in claim 2 wherein said selected reference point is located in the region of interest.

4. A method as defined in claim 2 wherein the step of determining said probe position and orientation includes determining one probe position and orientation for each of said plurality of images.

5. A method as defined in claim 2 wherein said echo signals represent multiple scan lines in each of said plurality of images and wherein the step of determining said probe position and orientation includes determining one probe position and orientation for each of said scan lines.

6. A method as defined in claim 1 wherein the step of transforming the echo signals and the determined probe position and orientation to image signals includes directly converting the echo signals to image signals that are referenced to said selected reference point.

7. A method as defined in claim 1 wherein the step of transforming echo signals and the determined probe position and orientation to image signals includes the steps of converting the echo signals to intermediate image signals representative of an intermediate image that is referenced to said probe position and orientation, and converting said intermediate image signals to said image signals that are referenced to said selected reference point.

8. A method as defined in claim 1 wherein the step of determining said probe position and orientation includes sensing said probe position and orientation.

9. A method as defined in claim 8 wherein the step of sensing said probe position and orientation includes sensing said probe position and orientation with a magnetic space tracking device.

10. A method as defined in claim 1 wherein the step of determining said probe position and orientation includes determining said probe position and orientation by analysis of the echo signals.

11. Apparatus for ultrasound imaging of a region of interest of a patient, comprising:
   a real-time ultrasound scanning system, including an ultrasound probe for ultrasonically scanning the region of interest, when the ultrasound probe is positioned at a selected probe position and orientation relative to the region of interest, by transmitting an ultrasound beam from said ultrasound probe, automatically steering the ultrasound beam with respect to said ultrasound probe and generating echo signals representative of ultrasound echoes received from the region of interest in response to the transmitted ultrasound beam, said echo signals being referenced to said probe position and orientation;
   a device for determining said probe position and orientation relative to a selected reference point;
   a scan converter responsive to said real-time ultrasound scanning system and said device for transforming the echo signals and the determined probe position and orientation into image signals representative of an image of the region of interest that is referenced to said selected reference point; and
   a display unit responsive to said image signals for displaying said image.

12. Apparatus as defined in claim 11 wherein said scan converter includes means for transforming the echo signals and the determined probe position and orientation into signals representative of a plurality of images that are referenced to said selected reference point as the probe position and orientation changes.

13. Apparatus as defined in claim 12 wherein said device for determining said probe position and orientation includes means for determining one probe position and orientation for each of said plurality of images.

14. Apparatus as defined in claim 12 wherein said echo signals represent multiple scan lines in each of said plurality of images and wherein said device for determining said probe position and orientation includes means for determining one probe position and orientation for each of said scan lines.

15. Apparatus as defined in claim 11 wherein said scan converter includes means for directly converting said echo signals to said image signals.

16. Apparatus as defined in claim 11 wherein said scan converter includes a first scan converter for converting the said echo signals to intermediate image signals representative of an intermediate image that is referenced to said probe position and orientation, and a second scan converter for converting said intermediate image signals to said image signals.

17. Apparatus as defined in claim 11 wherein said device for determining said probe position and orientation comprises a sensing device.

18. Apparatus as defined in claim 17 wherein said sensing device comprises a magnetic space tracking device.

19. A method for ultrasound imaging of a region of interest of a patient, comprising the steps of:
 a) providing a real-time ultrasound scanning system including an ultrasound probe;
 b) selecting a reference point for imaging;
 c) positioning the ultrasound probe at selected probe positions and orientations relative to the region of interest;
 d) ultrasonically scanning the region of interest by transmitting an ultrasound beam from said ultrasound probe, automatically steering the ultrasound beam with respect to said ultrasound probe and generating echo signals representative of ultrasound echoes received from the region of interest in response to the transmitted ultrasound beam, said echo signals being referenced to said probe positions and orientations;
 e) determining each of said probe positions and orientations relative to said reference point;
 f) transforming the echo signals and the determined probe positions and orientations to image signals representative of images of the region of interest that are referenced to said selected reference point; and
 g) displaying said images.

20. A method as defined in claim 19 wherein the step of determining said probe positions and orientations includes sensing said probe positions and orientations.

* * * * *